(12) United States Patent
Hoshino et al.

(10) Patent No.: US 8,338,502 B2
(45) Date of Patent: Dec. 25, 2012

(54) POLYMERIZABLE FLUORINE-CONTAINING COMPOUND AND TREATED SUBSTRATE HAVING A HYDROPHILIC REGION AND A WATER REPELLENT REGION

(75) Inventors: Taiki Hoshino, Chiyoda-ku (JP); Yutaka Furukawa, Chiyoda-ku (JP)

(73) Assignee: Asahi Glass Company, Limited, Tokyo (JP)

(*) Notice: Subject to any disclaimer, the term of this patent is extended or adjusted under 35 U.S.C. 154(b) by 723 days.

(21) Appl. No.: 12/365,970

(22) Filed: Feb. 5, 2009

(65) Prior Publication Data
US 2009/0155549 A1    Jun. 18, 2009

Related U.S. Application Data

(63) Continuation of application No. PCT/JP2007/065773, filed on Aug. 10, 2007.

(30) Foreign Application Priority Data

Aug. 11, 2006 (JP) ................... 2006-219780

(51) Int. Cl.
 C08G 18/67  (2006.01)
 C08G 61/00  (2006.01)
 C08F 2/46   (2006.01)
 B05D 3/02   (2006.01)
 B41M 5/00   (2006.01)
 C07C 55/36  (2006.01)

(52) U.S. Cl. ......... 522/174; 522/88; 522/89; 428/195.7; 428/336; 562/850; 562/849; 430/270.1; 430/325; 427/385.5; 526/242; 526/245

(58) Field of Classification Search ............. 428/195.1, 428/336; 562/850, 849; 430/270.1, 325; 427/385.5; 522/174, 88, 89; 526/245, 242; 528/401
See application file for complete search history.

(56) References Cited

U.S. PATENT DOCUMENTS
5,085,975 A    2/1992  Mueller
(Continued)

FOREIGN PATENT DOCUMENTS
JP    61-22048    1/1986
(Continued)

OTHER PUBLICATIONS

Machine English translation JP 09-157326 (abstract only); Ozaki et al.*

(Continued)

*Primary Examiner* — Mark Eashoo
*Assistant Examiner* — Jessica Paul
(74) *Attorney, Agent, or Firm* — Oblon, Spivak, McClelland, Maier & Neustadt, L.L.P.

(57) ABSTRACT

To provide a polymerizable fluorine-containing compound useful for producing a treated substrate having a hydrophilic region and a water repellent region, of which the contrast is high on its surface, without requiring a special apparatus, high energy light, or irradiation with light for a long time.
A polymerizable fluorine-containing compound, which is a derivative of a polyhydric alcohol and comprises at least one following structure (A) and at least one following structure (B) in its molecule:
 structure (A): a structure wherein a compound having a fluoroalkyl group and a carboxyl group is bonded to one hydroxyl group of a polyhydric alcohol by an ester linkage,
 structure (B): a structure wherein a compound having an ethylenic double bond and a carboxyl group is bonded to one hydroxyl group of a polyhydric alcohol by an ester linkage or a structure wherein a compound having an ethylenic double bond and an isocyanate group is bonded to one hydroxyl group of a polyhydric alcohol by a urethane bond.

19 Claims, 3 Drawing Sheets

U.S. PATENT DOCUMENTS

| | | | |
|---|---|---|---|
| 5,624,974 A | | 4/1997 | Onishi et al. |
| 5,945,482 A | * | 8/1999 | Fukuchi et al. ............... 525/100 |
| 6,096,476 A | * | 8/2000 | Yanagida et al. .......... 430/270.1 |
| 2007/0066779 A1 | | 3/2007 | Otaguro et al. |
| 2009/0011227 A1 | | 1/2009 | Furukawa |

FOREIGN PATENT DOCUMENTS

| | | |
|---|---|---|
| JP | 4-221344 | 8/1992 |
| JP | 8-231647 | 9/1996 |
| JP | 9-157326 | 6/1997 |
| JP | 09-157326 * | 6/1997 |
| JP | 11-344804 | 12/1999 |
| JP | 2000-282240 | 10/2000 |
| WO | 2005-049667 | 6/2005 |

OTHER PUBLICATIONS

U.S. Appl. No. 12/966,105, filed Dec. 13, 2010, Furukawa.

U.S. Appl. No. 12/551,863, filed Sep. 1, 2009, Furukawa.

* cited by examiner (d)

(e)

(f)

(g)

(h)

POLYMERIZABLE FLUORINE-CONTAINING COMPOUND AND TREATED SUBSTRATE HAVING A HYDROPHILIC REGION AND A WATER REPELLENT REGION

CROSS-REFERENCE TO RELATED APPLICATIONS

This application is a continuation of U.S. national phase of International Application No. PCT/JP2007/65773 filed 10 Aug. 2007, which designates the U.S. and claims foreign priority to Japanese Application No. 2006-219780 filed 11 Aug. 2006, the entire contents of which are hereby incorporated by reference.

TECHNICAL FIELD

The present invention relates to a polymerizable fluorine-containing compound which is useful for producing a treated substrate having a hydrophilic region and a water repellent region on its surface, a composition containing the compound, the treated substrate and a process for producing a member on which a pattern of a functional material is formed by using the treated substrate.

BACKGROUND ART

Many functional thin films are practically used in the fields of semiconductor devices, displays and luminescent elements. Functional thin films are ones formed by disposing a material having a desired property at desired positions, followed by patterning. The functional thin films are used as wiring, electrodes, insulating layers, luminescence layers, optical thin films, etc.

For example, a photoresist pattern obtained by photolithography may be mentioned. However, process steps of the photolithography are complex, and utilization efficiency of energy, material, etc. is low. Further, there is a problem such that since the photolithography is carried out in a clean room, cost of facilities is expensive.

Specifically, as a method to solve the problems in the photolithography, an ink-jet print method has been proposed. However, in the ink-jet print method, position accuracy is low, and it is difficult to form a fine pattern. Under the circumstance, the following methods (1) and (2) have been proposes to improve the position accuracy by preliminarily forming on a substrate surface a base film having a water repellent region which repels ink and a hydrophilic region which accepts ink.

(1) As a method for forming a hydrophilic region and a water repellent region on a substrate surface, a method may be mentioned wherein a hydrophilic surface is coated with a water repellent material such as a fluorine containing silane coupling agent to form a water repellent thin film, and the water repellent material is decomposed by light irradiation and removed (Patent Document 1). In the substrate obtained by the above method, only a region irradiated with light can be made a hydrophilic surface.

(2) As a method of using ultraviolet ray having a long wavelength, known is such a method that by using a photocatalyst such as titanium oxide, a water repellent thin film is decomposed (Patent Document 2).

Patent Document 1: JP-A-2000-282240
Patent Document 2: JP-A-11-344804

DISCLOSURE OF THE INVENTION

Problems to be Solved by the Invention

In the above method (1), high energy light having a wavelength of less than 200 nm is required, and light irradiation is required for a long time. Further, special equipments such as a large facility, a vacuum apparatus and a high energy light source are required. Further, since a high energy light having a wavelength of at most 200 nm is used in the method, an organic compound in the thin film of the pattern is also decomposed, and the contrast between the hydrophilic region and the water repellent region in the pattern tends to be low. Also in the above method (2), there is a problem of decomposing an organic compound in the thin film.

It is an object of the present invention to provide a polymerizable fluorine-containing compound which is useful for producing a treated substrate having a hydrophilic region and a water repellent region, of which the contrast is high on a surface of a substrate with a low amount of light in a short time without requiring special equipments or high energy light, or irradiation with light for a long time. It is also an object of the present invention to provide the treated substrate. Further, it is an object of the present invention to provide a member on which a pattern of a functional material is formed by employing the treated substrate.

Means to Accomplish the Objects

The present invention provides the followings.

(1) A polymerizable fluorine-containing compound, which is a derivative of a polyhydric alcohol and comprises at least one following structure (A) and at least one following structure (B) in its molecule:

structure (A): a structure wherein a compound having an $R^F$ group and a carboxyl group is bonded to one hydroxyl group of a polyhydric alcohol by an ester linkage, provided that the $R^F$ group is a fluoroalkyl group which may contain an etheric oxygen atom or a fluoroalkenyl group which may contain an etheric oxygen atom, structure (B): a structure wherein a compound having an ethylenic double bond and a carboxyl group is bonded to one hydroxyl group of a polyhydric alcohol by an ester linkage or a structure wherein a compound having an ethylenic double bond and an isocyanate group is bonded to one hydroxyl group of a polyhydric alcohol by a urethane bond.

(2) The polymerizable fluorine-containing compound according to the above (1), wherein the polyhydric alcohol is a saccharide or a saccharide derivative.

(3) The polymerizable fluorine-containing compound according to the above (1) or (2), wherein the structure (A) has a —$CF_2COO$— bond or a —$CF(CF_3)COO$— bond.

(4) The polymerizable fluorine-containing compound according to the above (1) to (3), which has at least three structures (B).

(5) A composition which comprises the polymerizable fluorine-containing compound as defined in the above (1) to (4) and a photopolymerization initiator.

(6) The composition according to the above (5), which contains a polyfunctional compound having at least four polymerizable functional groups, provided that the polyfunctional compound is a compound other than the above polymerizable fluorine-containing compound.

(7) A treated substrate having a hydrophilic region and a water repellent region on a surface of a substrate, characterized in that the water repellent region is made of a water repellent film formed by curing the composition as defined in the above (5) or (6).

(8) The treated substrate according to the above (7), wherein the difference in the contact angle to water between the water repellent region and the hydrophilic region is at least 50°.

(9) The treated substrate according to the above (7) or (8), wherein the difference in the contact angle to hexadecane between the water repellent region and the hydrophilic region is at least: 200.

(10) The treated substrate according to the above (7) to (9), wherein the water repellent film has a thickness of from 0.1 to 100 nm.

(11) The treated substrate according to the above (7) to (10), wherein the hydrophilic region and the water repellent region have a predetermined pattern.

(12) A process for producing a treated substrate having a hydrophilic region and a water repellent region on its surface, which comprises a step of forming a coating film containing the composition as defined in the above (5) or (6) on a surface of a substrate having a hydrophilic surface, a step of applying light on a part of the coating film surface to form a water repellent film by curing the composition and a step of removing an uncured composition present on the surface of the substrate in order to expose the hydrophilic surface.

(13) The process according to the above (12), wherein the substrate having a hydrophilic surface is a substrate obtained by hydrophilic treatment of its surface.

(14) The process according to the above (13), wherein light having a wavelength of at least 200 nm is applied.

(15) A process for producing a member on which a pattern of a functional material is formed, which comprises a step of coating the surface of the treated substrate as defined in the above (11) with a liquid containing a functional material in order to coat the hydrophilic region having a pattern of the treated substrate with the liquid and a step of drying it to form a pattern of the functional material.

(16) A process for producing a member on which a pattern of a functional material is formed, which comprises a step of coating the surface of the treated substrate as defined in the above (11) with a liquid containing a functional material in order to coat the hydrophilic region having a pattern of the treated substrate with the liquid, a step of drying it to form a pattern of the functional material and a step of removing the water repellent film.

(17) The process for producing a member according to the above (16), wherein the water repellent film is removed by washing using an alkali aqueous solution.

Effects of the Invention

By using the polymerizable fluorine-containing compound of the present invention, a treated substrate having a hydrophilic region and a water repellent region, of which the contrast is high on its surface can be produced, without using a large facility, a vacuum apparatus or a high energy light source. Namely, the treated substrate can be produced by using a simple apparatus and a simple light source with a low light amount in a short time.

Further, by using the treated substrate of the present invention, a member on which a pattern of a functional material is formed can be obtained, and the treated substrate of the present invention can be used for various applications.

EXPLANATION OF NUMERALS

Figure 1:
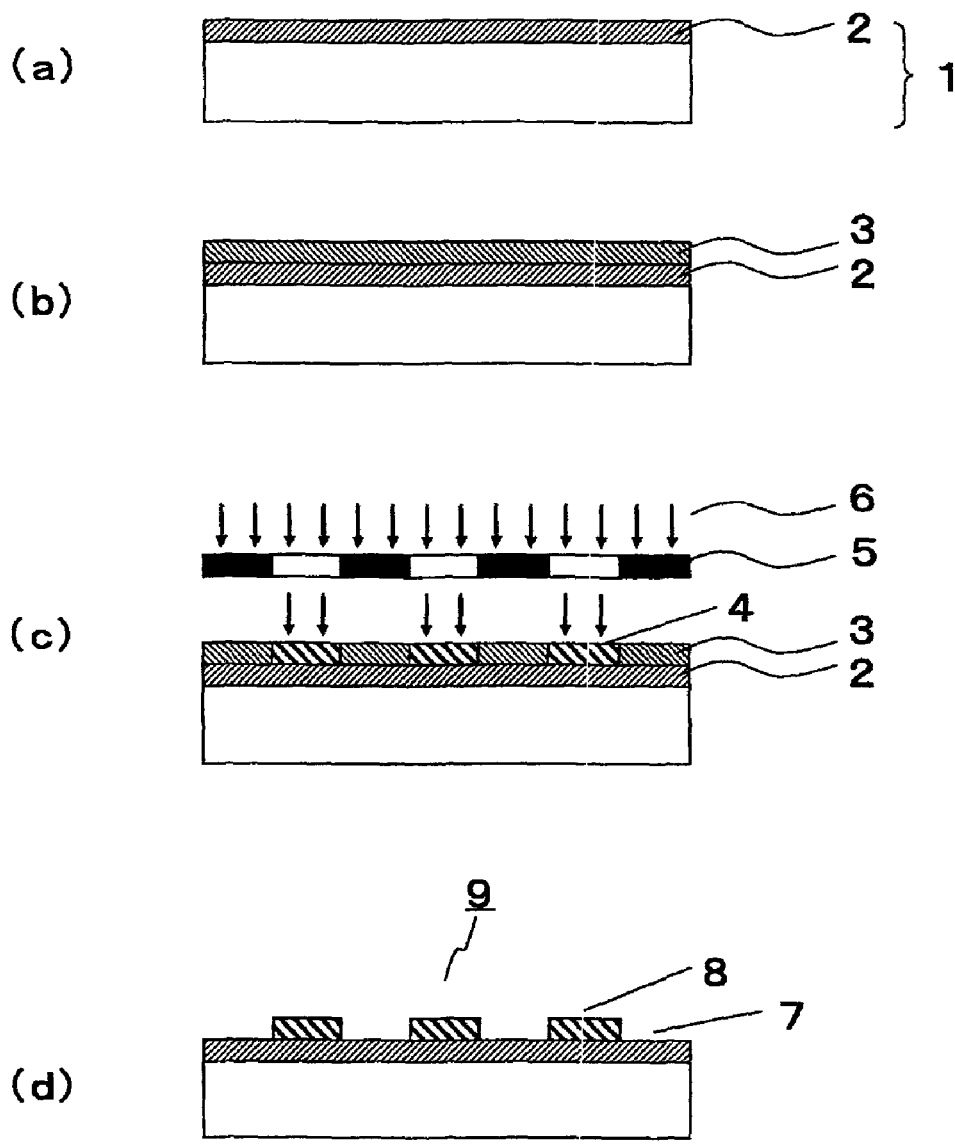
FIG. 1 is a cross sectional view showing one embodiment of the process for producing a treated substrate of the present invention.

1: Substrate
2: Hydrophilic surface
3: Coating film containing the composition of the present invention
4: Water repellent film
5: Photomask
6: Light
7: Hydrophilic region
8: Water repellent region
9: Treated substrate
10: Inkjet apparatus
11: Liquid containing a functional material
12: Functional material
13: Member on which a pattern of a functional material is formed

BEST MODE FOR CARRYING OUT THE INVENTION

Hereinafter, a polymerizable functional group selected from the group consisting of an acryloyl group and a methacryloyl group is referred to as "(meth)acryloyl group". Further, a (meth)acrylate means an acrylate or a methacrylate.
Polymerizable Fluorine-Containing Compound The polymerizable fluorine-containing compound of the present invention is a derivative of a polyhydric alcohol. As the polyhydric alcohol, the following may, for example, be mentioned:

An aliphatic polyhydric alcohol such as ethylene glycol, propylene glycol, trimethylene glycol, 1,4-butanediol, 2,3-butanediol, 1,5-pentanediol, 1,6-hexanediol, glycerol or pentaerythritol; or a dehydrocondensate of an aliphatic polyhydric alcohol such as diethylene glycol, triethylene glycol, tetraethylene glycol, dipropylene glycol, diglycerol, triglycerol, tetraglycerol, dipentaerythritol or tripentaerythritol.

A saccharide such as a monosaccharide (allose, arabinose, fructose, galactose, glucose, gulose, lyxose, mannose, rhamnose, ribose, sorbose, tagatose, talose, xylose, etc.), a disaccharide (cellobiose, lactulose, maltose, melibiose, parathinose, sucrose, trehalose, etc.) or an oligosaccharide (maltotriose, raffinose, cyclodextrin, etc.).

A saccharide derivative such as deoxy sugar (2-deoxyribose, 2-deoxygalactose, 2-deoxyglucose, fucose, etc.), an uronic acid (ascorbic acid, gluconic acid, lactobionic acid, etc.), an amino sugar (glucosamine, glucamine, etc.), a sugar alcohol (arabitol, erythritol, galactitol, sorbitol, inositol, mannitol, talitol, xylitol, maltitol, adonitol, etc.).

Among such polyhydric alcohols, an alcohol having at least four hydroxyl groups and of which solubility in an organic solvent is high, is preferred. If the solubility in an organic solvent is low, at a time of synthesizing a polyhydric alcohol derivative, volume efficiency deteriorates, and a large amount of a solvent is thereby required. As such a polyhydric alcohol, a cyclic polyhydric alcohol is preferred. The cyclic polyhydric alcohol is preferably a saccharide or a saccharide derivative, and among them, a disaccharide, an oligosaccharide and a sugar alcohol are preferred.

A compound having an $R^F$ group and a carboxyl group is bonded to one hydroxyl group of the polyhydric alcohol by an ester linkage, and to another hydroxyl group of the polyhydric alcohol, a compound having an ethylenic double bond and carboxyl group is bonded by an ester linkage, or a compound having an ethylenic double bond and an isocyanate group is bonded by an urethane bond. Therefore, the number of hydroxyl groups of the polyhydric alcohol is at least two, preferably at least four, more preferably at least six. The upper limit of the number of hydroxyl groups is not particularly limited, however, it is preferably about 20, more preferably at most 12.

Further, most of hydroxyl groups in the cyclic polyhydric alcohol are preferably bonded to the cyclic structure. Since such a hydroxyl group aligns towards the outside of its molecule, and an ethylenic double bond introduced into the hydroxyl group tends to be polymerized.

The polymerizable fluorine-containing compound of the present invention has at least one structure (A) wherein the compound having an $R^F$ group and a carboxyl group is bonded to one hydroxyl group of a polyhydric alcohol by an ester linkage.

The carbon number of the $R^F$ group is preferably from 1 to 12, more preferably from 3 to 12. The structure of the $R^F$ group may, for example, be a linear structure, a branched structure, a cyclic structure or a structure having a partially cyclic structure, and the linear structure or the branched structure is preferred. The $R^F$ group is preferably a group wherein at least two hydrogen atoms present in an alkyl group which may contain an etheric oxygen atom or an alkenyl group which may contain an etheric oxygen atom are substituted with fluorine atoms, more preferably a perfluoroalkyl group which may contain an etheric oxygen atom or a perfluoroalkenyl group which may contain an etheric oxygen atom.

As specific examples of the $R^F$ group, the following groups may be mentioned:
$F(CF_2)_3$—, $F(CF_2)_4$—, $F(CF_2)_5$—, $F(CF_2)_6$—, $F(CF_2)_7$—, $F(CF_2)_8$—$CF_3CF_2OCF_2$—, $CF_3CF_2OCF_2CF_2OCF_2$—, $CF_3CF_2CF_2OCF_2$—, $CF_3CF_2CF_2CF_2OCF_2$—, $CF_3CF_2CF_2OCF(CF_3)$— and $CF_3CF_2CF_2OCF(CF_3)CF_2OC(CF_3)$—.

In order to form the above structure (A), a carboxylic acid having an $R^F$ group, a carboxylic acid halide having an $R^F$ group or an acid anhydride having an $R^F$ group is preferably used. Among them, from the viewpoint of reactivity and availability, a carboxylic acid halide having an $R^F$ group, particularly a carboxylic acid fluoride having an $R^F$ group is preferred.

As the carboxylic acid fluoride having an $R^F$ group, the following compounds may be mentioned:
$F(CF_2)_3COF$, $F(CF_2)_4COF$, $F(CF_2)_5COF$, $F(CF_2)_6COF$, $F(CF_2)_7COF$, $F(CF_2)_8COF$, $CF_3CF_2OCF_2COF$, $CF_3CF_2OCF_2CF_2OCF_2COF$, $CF_3CF_2CF_2OCF_2COF$, $CF_3CF_2CF_2CF_2OCF_2COF$, $CF_3CF_2CF_2OCF(CF_3)COF$ and $CF_3CF_2CF_2OCF(CF_3)CF_2OCF(CF_3)COF$.

The above structure (A) preferably has a —$CF_2COO$— bond or a —$CF(CF_3)COO$— bond. Namely, as the carboxylic acid fluoride having an $R^F$ group, a terminal of the $R^F$ group bonded to the carboxyl group is preferably a —$CF_2$— or —$CF(CF_3)$—. As mentioned below, in the production of the member of the present invention on which a pattern of a functional material is formed, it is preferred that the ester bond of the structure (A) is to be easily hydrolyzed. When the ester bond is the —$CF_2COO$— bond or —$CF(CF_3)COO$— bond, the ester bond is to be easily hydrolyzed.

The polymerizable fluorine-containing compound of the present invention has at least one structure (B) wherein a compound having an ethylenic double bond and a carboxyl group is bonded to one hydroxyl group of a polyhydric alcohol by an ester linkage or a structure wherein a compound having an ethylenic double bond and an isocyanate group is bonded to one hydroxyl group of a polyhydric alcohol by an urethane bond. In order to form such a structure, the following methods (1) and (2) may be mentioned.

(1) A method for forming an ester linkage to a hydroxyl group in a polyhydric alcohol by using a carboxylic acid having an ethylenic double bond, a carboxylic acid chloride having an ethylenic double bond or an acid anhydride having an ethylenic double bond, as a compound having an ethylenic double bond.

(2) A method for forming an urethane bond to a hydroxyl group in a polyhydric alcohol by using a compound having an ethylenic double bond and an isocyanate group, as a compound having an ethylenic double bond.

The carboxylic acid having an ethylenic double bond may, for example, be acrylic acid, methacrylic acid, vinylacetic acid, crotonic acid, itaconic acid, maleic acid, fumaric acid or cinnamic acid.

The carboxylic acid chloride having an ethylenic double bond may, for example, be a (meth)acrylic acid chloride.

The acid anhydride having an ethylenic double bond may, for example, be maleic anhydride, itaconic anhydride, citraconic anhydride, methyl-5-norbornene-2,3-dicarbonic anhydride, 3,4,5,6-tetrahydrophtharic anhydride, cis-1,2,3,6-tetrahydrophtharic anhydride or 2-butenylsuccinic anhydride.

The compound having an ethylenic double bond and an isocyanate group may, for example, be 2-(meth)acryloyloxyethylisocyanate, 1,1-(bis(meth)acryloyloxymethyl)ethylisocyanate, or a 1:1 reaction product of a compound having a (meth)acryloyloxy group and a hydroxyl group with diisocyanate.

From the viewpoint of availability of materials, the above method (1) is preferred, and from the viewpoint of the easiness of the reaction, it is particularly preferred to use the carboxylic acid halide having an ethylenic double bond. In the case of using the carboxylic acid halide, the carboxylic acid fluoride having the $R^F$ group and the carboxylic acid halide are simultaneously or continuously reacted with a polyhydric alcohol, and the structure (A) and the structure (B) can be simultaneously or continuously formed, whereby production steps can be reduced.

The fluorine content in the polymerizable fluorine-containing compound of the present invention is preferably from 20 to 60 mass %, more preferably from 30 to 50 mass %. As mentioned hereinafter, a film formed by curing a composition containing the polymerizable fluorine-containing compound has both water repellency and oil repellency. If the fluorine content is too low, the water repellency and the oil repellency of the film formed by curing the composition containing the polymerizable fluorine-containing compound may sometimes deteriorate. If the fluorine content is too high, the water repellency and the oil repellency are excellent, however, the solubility in an organic solvent deteriorates, and it may sometimes be difficult to apply it on a substrate.

From the above viewpoints, the polymerizable fluorine-containing compound of the present invention preferably has at least two structures (A) in its molecule.

The polymerizable fluorine-containing compound of the present invention preferably has at least three structures (B), more preferably at least four structures (B) in its molecule. The more the number of the ethylenic double bonds in the polymerizable fluorine-containing compound is, the higher the probability of the reaction of the compound becomes, whereby the curing sensitivity by light irradiation becomes high.

From the above viewpoints, the polymerizable fluorine-containing compound of the present invention preferably has at least two structures (A) and at least three structures (B) in its molecule.

Further, in the polymerizable fluorine-containing compound of the present invention, an unreacted hydroxyl group may remain in the molecule.

Composition

The composition of the present invention contains the polymerizable fluorine-containing compound and a photopolymerization initiator.

The photopolymerization initiator is a material which initiates a polymerization reaction by absorbing light and generating radicals, and selected from materials which can initiate a polymerization reaction of a (meth)acryloyl group. For example, 2-hydroxy-2-methyl-1-phenylpropan-1-one (DAROCURE 1173, manufactured by Merck Ltd.), 1-hydroxycyclohexylphenylketone (IRGACURE184, manufactured by Ciba Specialty Chemicals K.K.), 1-(4-isopropylphenyl)-2-hydroxy-2-methylpropan-1-one (DAROCURE 1116, manufactured by Merck Ltd.), benzyldimethylketal (IRGACURE651, manufactured by Ciba Specialty Chemicals K.K.), 2-methyl-1-[4-methylthio)phenyl]-2-morpholinopropan-1-one (IRGACURE907, manufactured by Ciba Specialty Chemicals K.K.), 2-benzyl-2-dimethylamino-1-(4-morpholinophenyl)-butanone-1 (IRGACURE369, manufactured by Ciba Specialty Chemicals K.K.) or 2,4-diethylthioxanthone (KAYACURE DETX-S, manufactured by Nippon Kayaku Co., Ltd.) may preferably be mentioned. They can be used alone or two or more of them may be used in combination. The amount of the photopolymerization initiator is preferably from 0.1 to 50 mass %, more preferably from 1 to 10 mass %, based on the total amount of the polymerizable fluorine-containing compound.

Since it is effective to promote curing the composition, the composition of the present invention preferably contains a polyfunctional compound having at least four polymerizable functional groups, provided that the polyfunctional compound is a compound other than the above polymerizable fluorine-containing compound. Particularly in a case where a compound having at most three ethylenic double bonds is used as the polymerizable fluorine-containing compound, the above polyfunctional compound is particularly preferably contained. Even in a case where a compound having at least four ethylenic double bonds is used as the polymerizable fluorine-containing compound, the above polyfunctional compound is preferably contained. The polymerizable functional group in the polyfunctional compound is preferably a (meth)acryloyl group.

As preferred examples of the polyfunctional compound, pentaerythritol tetra(meth)acrylate, dipentaerythritol penta(meth)acrylate, dipentaerythritol hexa(meth)acrylate and ditrimethylolpropane tetra(meth)acrylate may, for example, be mentioned. The amount of the polyfunctional compound in the composition is preferably from 0.1 to 10 mass %, more preferably from 5 to 50 mass %, based on the total amount of the polymerizable fluorine-containing compound. If the amount of the polyfunctional compound is excessive, the water repellency on the water repellent region of a film formed by curing the composition may sometimes deteriorate.

A Treated Substrate Having a Hydrophilic Region and a Water Repellent Region

By using the composition of the present invention, a treated substrate having a hydrophilic region and a water repellent region on its surface can be produced. The treated substrate of the present invention can be produced by a step of forming a coating film containing the composition of the present invention on a surface of a substrate having a hydrophilic surface, a step of applying light on a part of the coating film surface to cure the composition to form a water repellent film and a step of removing an uncured composition present on the surface of the substrate in order to expose the hydrophilic surface.

The treated substrate of the present invention may, for example, be produced by the following steps 1 to 4 as shown in FIG. 1.

Step 1: A step of hydrophilic treatment of a surface of substrate 1 to make the surface be a hydrophilic surface 2 (FIG. 1(a)).

Step 2: A step of forming a coating film 3 containing the composition of the present invention on the surface 2 (FIG. 1(b)).

Step 3: A step of irradiating a part of the surface of the coating film 3 with light 6 to cure the composition to form a water repellent film 4 (FIG. 1(c)).

Step 4: A step of removing an uncured composition present on the surface of the substrate in order to expose the hydrophilic surface (FIG. 1(d)).

Step 1

Although in a case where the surface of the substrate is hydrophilic, the step 1 can be omitted, it is preferred to carry out the hydrophilic treatment on the surface of the substrate. The substrate used in the present invention can be selected from substrates made of glass; a silicon wafer; a metal such as Pd, Pt, Ru, Ag, Au, Ti, In, Cu, Cr, Fe, Zn, Sri, Ta, W or Pb; a metal oxide such as PdO, $SnO_2$, $In_2O_3$, PbO or $Sb_2O_3$; a boride such as $HfB_2$, $ZrB_2$, $LaB_6$, $CeB_6$, $YB_4$ or $GdB_4$; a carbide such as TiC, ZrC, HfC, TaC, SiC or WC; a nitride such as TiN, ZrN or HfN; a semiconductor such as Si or Ge; carbon and a resin such as a polyimide, a polystyrene, a polyethylene terephthalate or a polytetrafluorethylene. The glass, the silicon wafer, the metal oxide and the polyimide are preferred.

The shape of the substrate is not particularly limited and it preferably has a flat surface, a curved surface or a flat surface having a partially curved surface, and a flat surface is more preferred. Further, the surface area of the substrate is not particularly limited, and as far as conventional coating methods can be applied, the surface area of a substrate is not limited. Further, the surface treatment of the substrate of the present invention is preferably carried out on one surface of a flat substrate.

It is preferred to preliminarily clean the surface of a substrate by washing for producing a treated substrate. It is also preferred to subject the surface of the substrate to hydrophilic-treatment, and further it is also preferred to use a substrate having a hydrophilic film on its surface. Such surface treatments can be carried out by common methods, and in some cases, it is difficult to distinguish such treatments. In the present specification, all such treatments are regarded as the hydrophilic treatment, and the hydrophilic treatment will be described below.

As a method for hydrophilic-treating the surface of a substrate, conventional methods for washing the surface of plastics, metals, glass, ceramics, etc. can be employed. The washing method may, for example, be a method of wet-washing the surface of a substrate, a method of wet-oxidizing the surface of a substrate, a method of photo-washing the surface of a substrate, a method of photo-oxidizing the surface of a substrate, a method of coating the surface of a substrate with a hydrophilic compound or a combination thereof. A substrate having a hydrophilic surface can be used as it is, however, such a substrate usually tends to be stained. Therefore, it is preferred to preliminarily subject the substrate to hydrophilic treatment by wet-washing, photo-washing or a combination thereof before use. In a case where a material of a substrate is hydrophobic, it is preferred to subject the substrate surface to hydrophilic treatment by wet-oxidizing, photo-oxidizing or applying a hydrophilic compound.

For the wet-washing of the substrate, water, a water type detergent or a non-water type detergent (an organic solvent, a fluorine type solvent, etc.) may be used. Particularly, a method is preferred wherein the substrate is washed with water or a water type detergent containing a surfactant, and then the substrate is dried, while contaminants, moisture, etc. on its surface are removed by using an organic solvent having a low boiling point such as isopropyl alcohol or ethyl alcohol. Further, depending on the type of the substrate, or the type or degree of stain, a step may be added, or a part of step may be omitted. It is preferred that in order to wet-wash a substrate stained with an organic matter, the substrate is preliminarily washed with a fluorine type solvent such as dichloropentafluoropropane (AK-225, manufactured by Asahi Glass Company, Limited: a mixture of $CF_3CF_2CHCl_2$ and $CClF_2CF_2CHClF$) to remove the stain, and then the substrate is immerse-washed with a water type detergent or an organic detergent. At the time of the immerse-washing, ultrasonic washing may be carried out in combination. In the case of glass, instead of the immerse-washing or with the immerse-washing, a method of polish washing with an abrasive containing cerium oxide is fine particles, followed by rinsing the substrate with pure water and then air-drying may be employed.

In the wet-oxidizing the substrate, the surface is oxidized by using an aqueous solution of an oxidizing agent such as peroxide. The oxidizing agent is not particularly limited, and sulfuric acid, nitric acid, hydrogen peroxide, potassium persulfate, ammonium persulfate and potassium permanganate may, for example, be mentioned. The method of wet-oxidizing the substrate is not particularly limited so long as the substrate surface can be coated with the aqueous solution, and a spin coating method, a dip coating method, a spray coating method or a roll coating method may, for example, be employed.

As the method of photo-washing or photo-oxidizing the substrate, UV treatment, $UV/O_3$ treatment, plasma treatment, corona discharging treatment and flame treatment may, for example, be mentioned, and the $UV/O_3$ treatment is preferred.

Further, only by the wet-washing, fine organic stains (for example, residues of the surfactant in a detergent or suspended matters in the clean room) are likely to remain. Whereas, the above photo-washing is free from the problem of the fine organic stains. Accordingly, a method is preferred wherein at first, relatively large stains are removed by the wet-washing, and then the substrate is washed by the photo-washing.

The hydrophilic compound which may be used in the hydrophilic treatment of the substrate surface may, for example, be a hydrophilic polymer such as a poly(vinyl alcohol), a poly(vinyl pyrrolidone) or a poly(ethylene glycol), or a polyhydric alcohol such as glycerol, pentaerythritol or sorbitol. The compound for hydrophilic treatment which reacts on the substrate surface and forms a hydrophilic residue such as a silanol group on the surface may, for example, be a silane compound having a hydrolyzable group such as $Si(OCH_3)_4$, $Si(OCH_2CH_3)_4$, $[(CH_3)_3Si]_2NH$, $H-Si(OCH_2CH_3)_3$ or $NH_2CH_2CH_2CH_2-Si(OCH_2CH_3)_3$, a compound having said compound partially or entirely hydrolyzed, or a hydrolytic condensate of said compound.

It is preferred that the hydrophilic compound is applied in the form of a solution dissolved in a solvent. The hydrophilic polymer and this polyhydric alcohol are preferably dissolved in water, and the silane compound is preferably dissolved in an alcohol solvent such as isopropyl alcohol. The concentration of the hydrophilic compound in the solution is preferably from 0.01 to 10 mass %, more preferably from 0.1 to 1 mass %.

The method of coating on the substrate is not particularly limited, and a spin coating method, a dip coating method, a spray coating method, a roll coating method, a meniscus coating method and a screen printing method may be employed.

In a case where the surface of the substrate is made of various different materials, it is preferred to employ a method of coating the surface of the substrate with a hydrophilic compound as the hydrophilic treatment. Because, the same hydrophilic property can be imparted to the surface made of various materials.

Step 2

In order to form a coating film containing the composition of the present invention on a hydrophilic surface of a substrate, it is preferred to dry the substrate after coating the substrate with the composition. The composition is applied preferably in the form of a solution containing a solvent. The solvent is preferably an alcohol such as methanol, ethanol or isopropanol, an ester such as ethyl acetate or butyl acetate or a hydrocarbon such as hexane. The solid component concentration in the solution is preferably from 0.01 to 50 mass %, more preferably from 0.1 to 10 mass %.

As the coating method, a spin coating method, a dip coating method, a wire bar coating method, a blade coating method or a roll coating method may be employed. The coating may be carried out at room temperature or under heating. Further, after the coating, the substrate is preferably dried in air, under nitrogen stream or the like. The drying is preferably carried out at room temperature. In a case where the drying is carried out under heating, it is preferred that the temperature and time are adjusted, depending on the heat resistance of the material of the substrate.

Step 3

After a film is formed, a part of the film is irradiated with light. Light used for irradiation preferably has a wavelength of at least 200 nm, more preferably a wavelength of at least 300 nm. Further, light having a wavelength of at most 380 nm is preferred, and light having a wavelength of at most 365 nm is more preferred. When the wavelength of light is at least 200 nm, decomposition of the substrate can be prevented in most cases. Further, a photopolymerization initiator which initiates polymerization with light having a wavelength of at most 380 nm is easily available, and the light source is also not expensive. Irradiation time is properly changed, depending on the wavelength of light, the intensity of light, the type of light, the type of the composition, etc. In a case of an ultrahigh-pressure mercury lamp, irradiation time is from 5 to 120 seconds with from 2 to 100 mw/cm$^2$. In general, irradiation time with a high-pressure mercury lamp is shorter than that with an ultrahigh-pressure mercury lamp.

As the light source, a low-pressure mercury lamp, a high-pressure mercury lamp, an ultrahigh-pressure mercury lamp, a xenon lamp, a sodium lamp, a gas laser of e.g. nitrogen, a liquid laser of an organic dye solution or a solid laser of an inorganic single crystal having a rare earth element ion incorporated, may, for example, be mentioned. Further, as a light: source other than a laser capable of providing a monochromatic light, a light having a desired wavelength, which is obtained by subjecting a broadband line spectrum or a continuous spectrum to an optical filter such as a band-pass filter or a cut-off filter, may be used. Since a large area can be irradiated with light at once, a high-pressure mercury lamp or an ultrahigh-pressure mercury lamp is preferred as the light source.

Light irradiation is preferably carried out through a photomask. By this method, the curing reaction can be carried out only at a desired region on the film surface, and a treated substrate on which a desired pattern of a hydrophilic region and a water repellent region is formed can be obtained. Although the desired pattern is different depending on application, the desired pattern in the present invention may, for example, be a repeating pattern of lines, dots, rings, lattices, honeycombs or the like or a pattern of wirings, electrodes, insulating layers and light-emission layers, and their distance may, for example, be from 0.5 μm to 1 cm.

The atmosphere for light irradiation can be optionally selected. In a case where a water repellent film having a thickness of at most 100 nm is formed by curing the composition, since cure inhibition due to oxygen may sometimes occur, light irradiation is preferably carried out under an inert gas atmosphere such as nitrogen. The inert gas may, for example, be a gas selected from nitrogen, argon, helium and carbon dioxide, and nitrogen gas is preferred, since it is inexpensive.

Light irradiation may be carried out from either side of the substrate, as long as light has a wavelength which can transmit through the substrate. Usually, it is preferred to apply light from the side of the film containing the composition.

If light or laser is applied though a photomask, a treated substrate on which a desired pattern of a hydrophilic region and a water repellent region is formed can be obtained. Further, it is possible to form a pattern such that the line width of the hydrophilic region and the water repellent region is at most 10 μm.

Step 4

After a water repellent film is formed by curing the composition, an uncured composition remained on the substrate surface is removed. By removing the uncured composition, the hydrophilic surface is exposed. As a method for removing the uncured composition, in a case where the molecular weight of the polymerizable fluorine-containing compound is low, it is preferred to remove the uncured composition by blowing nitrogen stream. In a case where the molecular weight of the polymerizable fluorine-containing compound is high, since the composition is not likely to evaporate, it is preferred to wash the surface on which the polymerizable fluorine-containing compound remains with an organic solvent. The organic solvent to be used for washing is preferably a solvent which dissolves the polymerizable fluorine-containing compound. The organic solvent may, for example, be an alcohol such as methanol, ethanol or isopropanol, an ester such as ethyl acetate or butyl acetate or a hydrocarbon solvent such as hexane.

As mentioned above, a treated substrate having a hydrophilic region and a water repellent region on a surface of a substrate, can be provided. The hydrophilic region can be distinguished from the water repellent region by contact angle to water. In the present specification, the contact angle is represented by a measured value obtained by a sessile drop method.

The contact angle to water of the hydrophilic region is preferably at most 50°, more preferably at most 40°, particularly preferably at most 20°. The contact angle to water of the water repellent region is preferably at least 800, more preferably at least 100°, particularly preferably at least 110°.

The difference in the contact angle to water between the water repellent region and the hydrophilic region is preferably at least 50°, more preferably at least 70°, particularly preferably at least 80°.

Since the water repellent region of the treated substrate of the present invention is made of a water repellent film formed by curing a composition containing the polymerizable fluorine-containing compound of the present invention, the water repellent region also has a liquid repellency to organic solvents. Since the water repellent region has a liquid repellency to organic solvents, relatively the hydrophilic region has a lipophilic property to organic solvents.

The contact angle to hexadecane of the hydrophilic region is preferably at most 40°, more preferably at most 30°, particularly preferably at most 20°. The contact angle to hexadecane of the water repellent region is preferably at least 40°, more preferably at least 50°, particularly preferably at least 60°.

The difference in the contact angle to hexadecane between the water repellent region and the hydrophilic region is preferably at least 20°, more preferably at least 30°, particularly preferably at least 40°.

In a case where a liquid containing a functional material is applied as mentioned below, the higher the difference in the contact angle between the hydrophilic region and the water repellent region is, the more the liquid containing a functional material on both the water repellent region and the hydrophilic region tends to flow on the hydrophilic region, whereby on a pattern made of the functional material formed by drying the liquid containing a functional material, a pattern of a water repellent region and a hydrophilic region can accurately be realized.

Further, the smaller the contact angle of the hydrophilic region is, the better the liquid containing a functional material wettably spreads on the hydrophilic region, whereby the film thickness of a pattern made of a functional material formed by drying the liquid containing the functional material can be made uniform.

In the present invention, in a case where a flexible substrate such as a plastic substrate is used as the substrate, by irradiating the substrate with light by installing plural rolls and an exposure apparatus between the plural rolls so that Roll to Roll method can be carried out, a treated substrate can be obtained with a high throughput.

A Member on which a Pattern of a Functional Material is Formed

By using the treated substrate on which a desired pattern of a hydrophilic region and a water repellent region are formed, a member on which a pattern of a functional material is formed can be produced. The member of the present invention can be produced by a step of coating a surface of the treated substrate with a liquid containing a functional material in order to coat the hydrophilic region having a pattern of the treated substrate with the liquid, a step of drying it to form a pattern of the functional material and as a case requires, a step of removing the water repellent film.

Figure 2:
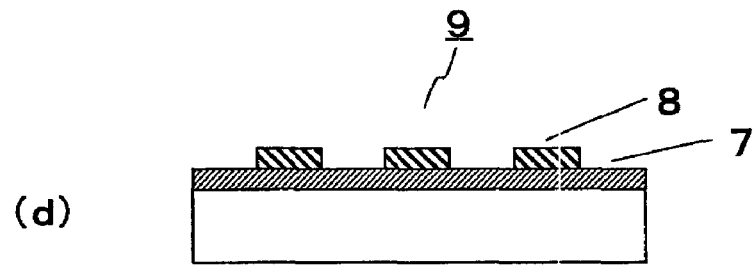
FIG. 2 is a cross sectional view showing one embodiment of the process for producing a member of the present invention.
Figure 2:
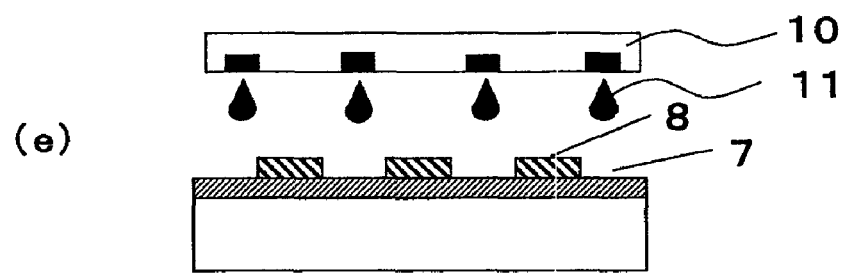
Figure 2:
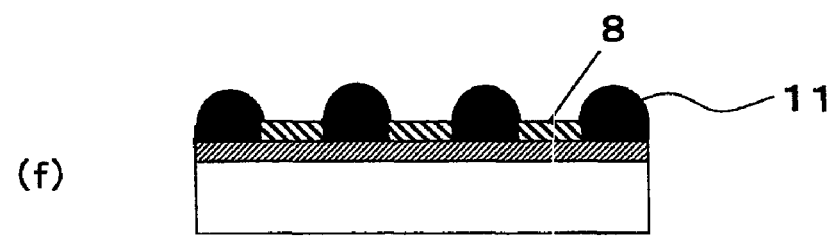
Figure 2:
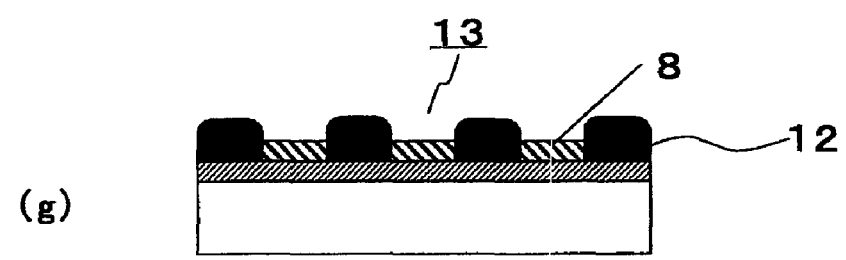
Figure 2:
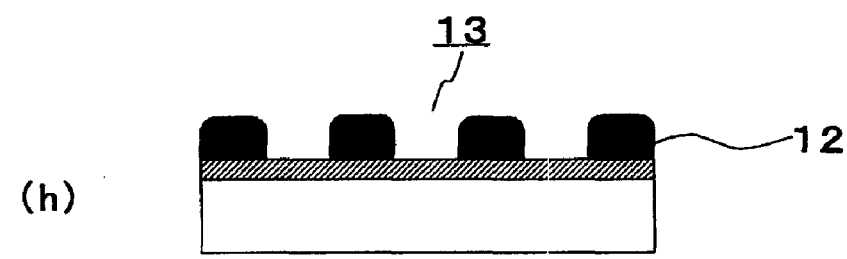
Figure 3:
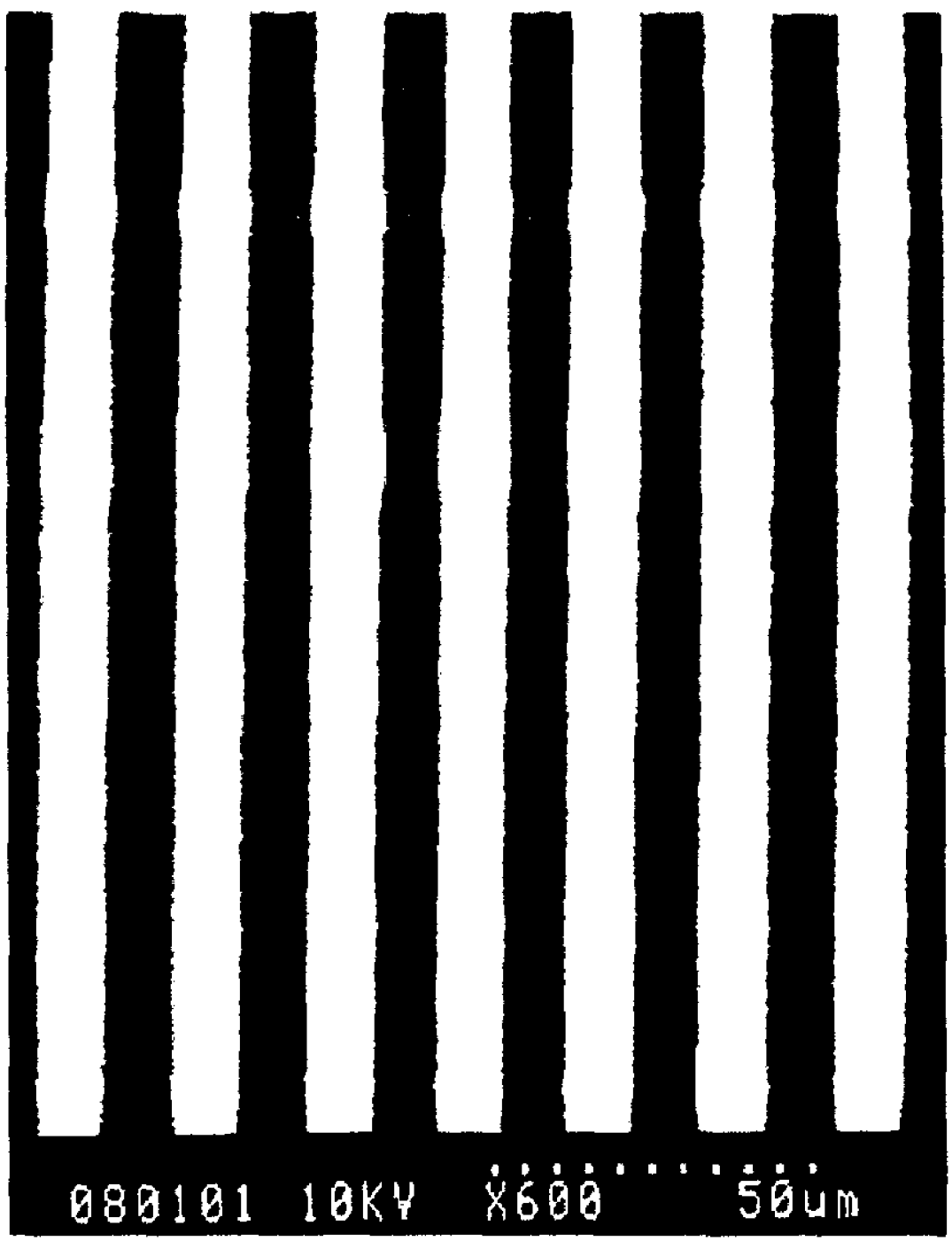
FIG. 3 is a SEM photograph of the treated substrate on which a water repellent pattern is formed in Examples.

The member on which a pattern made of a functional material of the present invention is formed, may, for example, be produced by the following steps 5 and 6, and, as a case requires, a step 7, as shown in FIG. 2.

Step 5: A step of coating a surface of a treated substrate 9 with a liquid 11 containing a functional material (FIG. 2(e)), and a step of applying the liquid 11 on a hydrophilic region 7 having a pattern of the treated substrate (FIG. 2(f)).

Step 6: A step of drying the substrate to form a pattern of a functional material 12 (FIG. 2(g)).

Step 7: A step of removing a water repellent region 8 made of a water repellent film 4 (FIG. 2(h)).

Step 5:

The functional material may, for example, be a metal particles-dispersed paste for forming metal wiring, a pigment material for forming a color filter, a ceramic material for forming an electronic device or an organic device or an organic semiconductor material.

The liquid containing a functional material means a liquid wherein a functional material is dissolved or dispersed in water, an organic solvent or a mixture thereof. Since as mentioned above, the water repellent region on the treated substrate of the present invention has an oil repellency, as the above organic solvent, a low polar organic solvent may be used. The organic solvent is not particularly restricted, and may, for example, be an alcohol such as methanol, ethanol, propanol or butanol; a hydrocarbon such as n-pentane, n-hexane, n-heptane, n-octane, decane, dodecane, tetradecane, hexadecane, octadecane, cyclohexane, toluene, xylene, tetrahydronaphthalene or decahydronaphthalene; an ether compound such as ethylene glycol dimethyl ether, ethylene glycol diethyl ether, ethylene glycol methylethyl ether, diethylene glycol dimethyl ether, diethylene glycol diethyl ether, diethylene glycol methylethyl ether, tetrahydrofuran or dioxane; or a polar compound such as propylene carbonate, γ-butyrolactone, N-methyl-2-pyrrolidone, dimethylformamide, dimethylsulfoxide or cyclohexanone. Among them, from the viewpoints of solubility, dispersability and their stability, it is preferred to select an appropriate solvent. Such an organic solvent may be used alone, or two or more solvents may be used in combination.

The coating method may, for example, be a coating method such as spin coating, dip coating, wire bar coating, blade coating or roll coating, or a printing method for a specific region such as screen printing or inkjet printing. Among them, from the viewpoint of selectively coating the hydrophilic region on the pattern of the water repellent region and the hydrophilic region, the screen printing or the inkjet printing is preferred.

Step 6:

By drying the substrate after the coating and removing the solvent used in step 5, a member on which a pattern of a functional material is formed can be obtained. The drying is preferably carried out in atmosphere, nitrogen stream or the like. Further, the drying is preferably carried out at room temperature or under heating. In a case where the drying is carried out under heating, it is preferred that the temperature and the time are optionally changed, depending on the heat resistance of a material of a substrate.

Step 7:

The member on which the pattern of the functional material is formed and from which the water repellent film is further removed is useful as an electronic element. The water repellent film is removed, because in a case where the member is used as an electric element, the water repellent film may influence the operation of the element.

It is preferred to remove the water repellent film by washing by using an alkaline aqueous solution. The reason why the water repellent film can be removed with the alkaline aqueous solution is not clear, however, the present inventors consider as follows. In the present invention, a polymer of a polymerizable fluorine-containing compound is present on the water repellent film. The polymer has a structure (A) wherein a compound having an $R^F$ group and a carboxyl group is bonded by an ester linkage, and the ester linkage is hydrolyzed under an alkaline condition, whereby a salt of a carboxylic acid having an $R^F$ group and alcohol are formed. The salt of a carboxylic acid having an $R^F$ group dissolves in water. The alcohol is a part of the polymer, however, since it is a polyhydric alcohol, it can be solved in water. The alkaline aqueous solution may, for example, be an aqueous solution or a methanol solution of an alkali metal hydroxide (such as sodium hydroxide or potassium hydroxide), or an aqueous solution or a methanol solution of tetramethylammonium hydroxide. Among them, an aqueous solution of sodium hydroxide is preferred.

From the viewpoint of the easiness of removing as mentioned above, the thickness of the water repellent film is preferably thin. It is preferably from 0.1 to 100 nm, more preferably from 0.1 to 50 nm, particularly preferably from 0.1 to 10 nm.

EXAMPLES

Now, the present invention will be described in further detail with reference to Examples, but it should be understood that the present invention is by no means restricted thereto.

Example 1

Synthesis of Polymerizable Fluorine-Containing Compound (a)

1.0 g of sucrose, 3.0 g of triethylamine and 10 mg of hydroquinone as a polymerization inhibitor were dissolved in 50 mL of dimethylformamide in a 200 mL three necked flask. Under cooling with ice, 4 equivalent amount of acryloylchloride was dropwise added slowly to 1 equivalent amount of sucrose. After stirring for one hour at room temperature, under cooling with ice, 4 equivalent amount of perfluorocarboxylic acid fluoride $CF_3CF_2CF_2OCF(CF_3)COF$ was slowly dropwise added. Further, the mixture was stirred at room temperature for 3 hours, 100 mL of distilled water was added, and 50 mL of dichloropentafluoropropane (tradename AK-225, manufactured by Asahi Glass Co., Ltd., hereinafter referred to as R225) was added for extraction. The extracted solution was washed with 100 mL of distilled water three times, and the solvent was distilled off to obtain a product.

The ratio (molar ratio) of acryloyl groups to $CF_3CF_2CF_2OCF(CF_3)CO-$ groups in the product was calculated as follows, from the internal analyses by $^1$H-NMR and $^{19}$F-NMR. As the internal standard substance, 1,3-bis(trifluoromethyl)benzene was used. The content of the acryloyl groups was obtained from an integral ratio of proton (4H) bonded to a benzene ring of the internal standard substance and proton (3H) of the acryloyl group of 5.9 to 6.5 ppm by $^1$H-NMR. Further, the content of the $CF_3CF_2CF_2OCF(CF_3)CO-$ groups was obtained from an integral ratio of fluorine (6F) in the internal substance and fluorine in the $CF_3CF_2CF_2OCF(CF_3)CO-$ groups by $^{19}$F-NMR. Table 1 shows the total amount of ratio as the number of hydroxyl groups in a polyhydric alcohol which is a starting material.

Examples 2 to 6

Synthesis of Polymerizable Fluorine-Containing Compounds (b) to (f)

Polymerizable fluorine-containing compounds (b) to (f) were obtained in the same manner as in the synthesis of the polymerizable fluorine-containing compound (a), except that type of the polyhydric alcohol, the amount of acryloyl chloride and the type and amount of the perfluorocarboxylic acid fluoride were changed as shown in Table 1.

TABLE 1

| Ex. | Compound | Polyhydric alcohol | CH$_2$=CHCOCl equivalent amount | R$^F$COF Type | R$^F$COF Equivalent amount | Ratio (molar ratio) of CH$_2$=CHCO groups to R$^F$ groups in product |
|---|---|---|---|---|---|---|
| 1 | a | Sucrose | 4 | x | 4 | 4.2:3.8 |
| 2 | b | Sucrose | 5 | x | 3 | 5.3:2.7 |
| 3 | c | Sucrose | 6 | x | 2 | 6.1:1.9 |
| 4 | d | Sucrose | 3 | y | 5 | 3.4:4.6 |
| 5 | e | Sucrose | 6 | y | 2 | 6.0:2.0 |
| 6 | f | Sorbitol | 3 | x | 3 | 2.9:3.1 |

Here, in Table 1, perfluorocarboxylic acid fluoride means the following compounds.
x: $CF_3CF_2CF_2OCF(CF_3)COF$,
y: $CF_3CF_2CF_2OCF(CF_3)CF_2OCF(CF_3)COF$.

Example 7

Preparation of a Composition 2.5 g of isopropanol (hereinafter referred to as "IPA") as a solvent was added in a sample bottle, and 0.06 g of a 1% IPA solution of a polymerization initiator (IRGACURE 907, manufactured by CIBA-GEIGY Limited) was added thereto. 0.1 g of a 10% solution (solvent: IPA) of the polymerizable fluorine-containing compound (a) was added thereto. The sample bottle was shaken a few times to mix the solution, and a composition (a1) was thereby prepared. The composition was used as a coating solution in the following steps.

Examples 8 to 16

Preparation of a Coating Solution

Respective compositions shown in Table 2 were obtained in the same manner as in the preparation of the composition 1 except that type of the polymerizable fluorine-containing compound, the solvent, and whether the dipentaerythritolhexaacrylate solution is added or not were changed as shown in Table 2. Further, adding the dipentaerythritolhexaacrylate solution means that for preparing a composition, 0.2 c of 1% IPA solution of dipentaerythritolhexaacrylate (hereinafter referred to as DPHA) was added.

TABLE 2

| Ex. | Composition | Compound/solvent | DPHA addition |
|---|---|---|---|
| 7 | a1 | a/IPA | Not added |
| 8 | a2 | a/IPA | Added |
| 9 | b1 | b/IPA | Not added |
| 10 | b2 | b/IPA | Added |
| 11 | c1 | c/IPA | Not added |
| 12 | c2 | c/IPA | Added |
| 13 | d1 | d/R225 | Added |
| 14 | e1 | e/R225 | Not added |
| 15 | e2 | e/R225 | Added |
| 16 | f1 | f/R225 | Added |

Example 17

Preparation of a Treated Substrate Base Plate Wash

A 5 cm×5 cm silicon wafer was washed with ethanol and then washed with UV/O$_3$.

Coating with a Composition

After washing the silicon wafer, the silicon wafer was coated with the compositional prepared in Example 7 by spin coating under a condition of 3000 rpm for 20 seconds, and a film was formed.

Light Irradiation

A surface of the obtained film was irradiated with light of a high-pressure mercury lamp under nitrogen atmosphere from the film side through a photomask having a pore pattern of 2.5 cm×5 cm. Among the following irradiation conditions, the condition 1 was selected.

Condition 1: Irradiation with light of 365 nm at intensity of 85 mw/cm$^2$ for 30 seconds Condition 2: Irradiation with light of 365 nm at intensity of 50 mw/cm$^2$ for 10 seconds Substrate Wash After the light irradiation, the substrate was rinsed with IPA, then rinsed with ethanol and dried under nitrogen stream, and a treated substrate was obtained.

Examples 18 to 28

Preparation of a Treated Substrate

Respective treated substrates were obtained in the same manner as in the preparation of a treated substrate in Example 17, except that the composition to be applied and the condition of light irradiation were changed as shown in Table 3.

Treated substrates obtained in Examples 17 to 28 were evaluated by the following manner.

Measurement of Contact Angle

Contact angles of the treated substrate to water and hexadecane were measured. The contact angle to water was measured by putting water droplets on 3 different spots on a surface of the substrate to be measured, and each droplet was measured in accordance with JIS R3257 "Testing method of wettability of glass substrate". The droplet was 2 μL/droplet, and the measurement was carried out at 20° C. The contact angle is represented by an average value of 3 droplets (n=3). The contact angle to hexadecane was also measured in the same manner. The results were shown in Table 3.

Removement of a Water Repellent Film with an Alkali Aqueous Solution

The treated substrate was washed with a sodium hydroxide aqueous solution, and degree of removement of the water repellent film was evaluated as shown below. The results are shown in Table 3.

⊚: When the substrate was washed with 0.1 mol/L sodium hydroxide aqueous solution, the contact angle to water was at most 10°.

◯: When the substrate was washed with 1.0 mol/L sodium hydroxide aqueous solution, the contact angle to water was at most 100.

X: When the substrate was washed with 1.0 mol/L sodium hydroxide aqueous solution, the contact angle to water was higher than 10°.

TABLE 3

| Ex. | Composition | Light irradiation condition | Contact angle (degree) | | | | Removing property of water repellent film |
|---|---|---|---|---|---|---|---|
| | | | Water | | Hexadecane | | |
| | | | Irradiation part | Shaded part | Irradiation part | Shaded part | |
| 17 | a1 | 1 | 108 | 17 | 61 | 24 | ◎ |
| 18 | a1 | 2 | 102 | 17 | 46 | 25 | ◎ |
| 19 | a2 | 1 | 104 | 32 | 62 | 29 | ◎ |
| 20 | a2 | 2 | 105 | 31 | 58 | 18 | ◎ |
| 21 | b1 | 1 | 102 | 7 | 59 | 19 | ◎ |
| 22 | b2 | 1 | 102 | 11 | 60 | 25 | ◎ |
| 23 | c1 | 1 | 98 | 28 | 49 | 16 | ◎ |
| 24 | c2 | 1 | 98 | 32 | 45 | 10 | ◎ |
| 25 | d1 | 1 | 111 | 12 | 62 | 18 | ○ |
| 26 | e1 | 1 | 108 | 25 | 58 | 12 | ○ |
| 27 | e2 | 1 | 108 | 31 | 60 | 18 | ○ |
| 28 | f1 | 1 | 105 | 23 | 59 | 22 | ◎ |

In Examples 17 to 28, the shape of the treated substrate having a hydrophilic region and a water repellent region was examined. In Examples 17 and 18 wherein DPHA was not added in the composition, as compared to Example 18 of which the amount of light irradiation was small, in Example 17 of which the light irradiation amount was large, the contact angle to hexadecane on a light irradiated part was high. Therefore, it is evident that in Examples 19 and 20 wherein DPHA was added in the composition, the influence of the amount of light irradiation was small.

Example 29

Comparative Example

A treated substrate was produced in the same manner as in Example 17 except that instead of applying the compositional, $CH_2=C(CH_3)COOCH_2CH_2CF_2CF_2CF_2CF_2CF_2CF_3$ was used. The contact angle was measured, however, the water repellency was not observed.

Example 30

Preparation of a Treated Substrate on which a Water Repellent and Hydrophilic Pattern is Formed A treated substrate having a pattern of a hydrophilic region and water repellent region was obtained in the same manner as in Example 17, except that at the time of light irradiation, a photomask of 10 µmL/S was used.

A surface of a sample was observed by SEM. The photograph is shown in FIG. 2. A light-dark pattern with a 10 µm width was formed. The film thickness of the water repellent region was measured by AFM, and the film thickness was from 6 to 11 nm, and the average value of 10 measured points was 8.3 nm.

INDUSTRIAL APPLICABILITY

According to the present invention, a fine pattern having a hydrophilic region and a water repellent region can be formed without employing a large facility, a vacuum apparatus or a high energy light source. In a case where a functional ink is spread on the pattern by using an ink-jet, since only the hydrophilic region is coated with the functional ink and the water repellent region is not coated with the functional ink, patterning can be carried out on a substrate with the functional ink. Further, the present invention can also be applied for forming electronic device circuits. Further, the thin film having the water repellent-hydrophilic pattern can be transcribed on another substrate by dyeing the hydrophilic region with a functional ink.

The entire disclosure of Japanese Patent Application No. 2006-219780 filed on Aug. 11, 2006 including specification, claims, drawings and summary is incorporated herein by reference in its entirety.

What is claimed is:

1. A polymerizable fluorine-containing compound, which is a derivative of a polyhydric alcohol and comprises at least one following structure (A) and at least one following structure (B) in its molecule:

structure (A): a structure wherein a compound having an $R^F$ group and a carboxyl group is bonded to one hydroxyl group of a polyhydric alcohol by an ester linkage, provided that the $R^F$ group is a fluoroalkyl group which may contain an etheric oxygen atom or a fluoroalkenyl group which may contain an etheric oxygen atom, structure (B): a structure wherein a compound having an ethylenic double bond and a carboxyl group is bonded to one hydroxyl group of a polyhydric alcohol by an ester linkage or a structure wherein a compound having an ethylenic double bond and an isocyanate group is bonded to one hydroxyl group of a polyhydric alcohol by a urethane bond, wherein the polyhydric alcohol is a saccharide or a saccharide derivative.

2. The polymerizable fluorine-containing compound according to claim 1, wherein the saccharide or a saccharide derivative is cyclic.

3. The polymerizable fluorine-containing compound according to claim 1, wherein the structure (A) has a —$CF_2COO$— bond or a —$CF(CF_3)COO$— bond.

4. The polymerizable fluorine-containing compound according to claim 1, which has at least three structures (B).

5. A composition which comprises the polymerizable fluorine-containing compound as defined in claim 1 and a photopolymerization initiator.

6. The composition according to claim 5, further comprising a polyfunctional compound having at least four polymerizable functional groups, provided that the polyfunctional compound is a compound other than the above polymerizable fluorine-containing compound.

7. A treated substrate having a hydrophilic region and a water repellent region on a surface of a substrate, characterized in that the water repellent region is made of a water repellent film formed by curing the composition as defined in claim 5.

8. The treated substrate according to claim 7, wherein the difference in the contact angle to water between the water repellent region and the hydrophilic region is at least 50°.

9. The treated substrate according to claim 7, wherein the difference in the contact angle to hexadecane between the water repellent region and the hydrophilic region is at least 20°.

10. The treated substrate according to claim 7, wherein the water repellent film has a thickness of from 0.1 to 100 nm.

11. The treated substrate according to claim 7, wherein the hydrophilic region and the water repellent region have a predetermined pattern.

12. A process for producing a treated substrate having a hydrophilic region and a water repellent region on its surface, which comprises a step of forming a coating film containing the composition as defined in claim 5 on a surface of a substrate having a hydrophilic surface, a step of applying light on a part of the coating film surface to form a water repellent film by curing the composition and a step of removing an uncured composition present on the surface of the substrate in order to expose the hydrophilic surface.

13. The process according to claim 12, wherein the substrate having a hydrophilic surface is a substrate obtained by hydrophilic treatment of its surface.

14. The process according to claim 13, wherein light having a wavelength of at least 200 nm is applied.

15. A process for producing a member on which a pattern of a functional material is formed, which comprises a step of coating the surface of the treated substrate as defined in claim 11 with a liquid containing a functional material in order to coat the hydrophilic region having a pattern of the treated substrate with the liquid and a step of drying it to form a pattern of the functional material.

16. A process for producing a member on which a pattern of a functional material is formed, which comprises a step of coating the surface of the treated substrate as defined in claim 11 with a liquid containing a functional material in order to coat the hydrophilic region having a pattern of the treated substrate with the liquid, a step of drying it to form a pattern of the functional material 5 and a step of removing the water repellent film.

17. The process for producing a member according to claim 16, wherein the water repellent film is removed by washing using an alkali aqueous solution.

18. The compound of claim 1, wherein the polyhydric alcohol is a saccharide.

19. A composition, comprising:
a photopolymerization initiator;
a polyfunctional compound having five or six polymerizable functional groups; and
a polymerizable fluorine-containing compound, which is a derivative of a polyhydric alcohol and comprises at least one following structure (A) and at least one following structure (B) in its molecule:
structure (A): a structure wherein a compound having an $R^F$ group and a carboxyl group is bonded to one hydroxyl group of a polyhydric alcohol by an ester linkage, provided that the $R^F$ group is a fluoroalkyl group which may contain an etheric oxygen atom or a fluoroalkenyl group which may contain an etheric oxygen atom,
structure (B): a structure wherein a compound having an ethylenic double bond and a carboxyl group is bonded to one hydroxyl group of a polyhydric alcohol by an ester linkage or a structure wherein a compound having an ethylenic double bond and an isocyanate group is bonded to one hydroxyl group of a polyhydric alcohol by a urethane bond,
wherein the polyfunctional compound is a compound other than the polymerizable fluorine-containing compound and wherein the polyhydric alcohol is a saccharide or a saccharide derivative.

* * * * *